United States Patent [19]

Renga

[11] Patent Number: 4,529,544

[45] Date of Patent: Jul. 16, 1985

[54] FORMATION OF AZETIDINES BY DECARBOXYLATION OF TETRAHYDRO-1,3-OXAZIN-2-ONES

[75] Inventor: James M. Renga, Midland, Mich.

[73] Assignee: The Dow Chemical Company, Midland, Mich.

[21] Appl. No.: 527,379

[22] Filed: Aug. 29, 1983

Related U.S. Application Data

[63] Continuation-in-part of Ser. No. 358,158, Mar. 15, 1982, abandoned.

[51] Int. Cl.$^3$ .................. C07D 205/04; C07D 265/10
[52] U.S. Cl. .................................. 260/239 A; 544/97
[58] Field of Search ................................. 260/239 AR

[56] References Cited

U.S. PATENT DOCUMENTS 3,649,618  3/1972  Horrom ....................... 260/239 AR
4,201,725  5/1980  Pigerol et al. ....................... 560/172
4,384,115  5/1983  Renga ................................... 544/97

OTHER PUBLICATIONS

CA 54: 3361-6z (1960).
CA 64: 16491f (1966).
CA 90: 152004a (1979).
CA 91: 39236k (1979).
Huff, *Physicians' Desk Reference*, 35th ed., Med. Econ. Co., Oradell, N.J., (1981), pp. 1670, 1801.
Huff, *Physicians' Desk Reference*, 38th ed., Med. Econ. Co., Oradell, N.J. (1984), pp. 514, 677, 695–696, 1358.
Keasling, J. Med. Chem., 14, 1106, (1971).
Virgona et al., Pestic. Sci., 7, 72, (1976).
Conia et al., Angew. Chem. Int. Ed. Eng., vol. 14, (1975), pp. 473–485.
Chem. Abstracts, vol. 56(1), p. 452 at column i "3-Substituted Azetidines".
Weissberger ed., Heterocyclic Comp. with Three- and Four-Membered Rings (Pt.t2), Interscience (1964), pp. 920–921.
H. C. van der Plas, *Ring Transformations of Heterocycles*, vol. 2, Academic Press, London and N.Y., (1973), pp. 188–189.
N. H. Cromwell et al., Chem. Rev., 79(4), 331–358, (1979).

*Primary Examiner*—Donald G. Daus
*Assistant Examiner*—William A. Teoli, Jr.
*Attorney, Agent, or Firm*—Douglas N. Deline; Christopher J. Rudy

[57] ABSTRACT

Azetidines are prepared by decarboxylating a tetrahydro-1,3-oxazin-2-one.

9 Claims, No Drawings

FORMATION OF AZETIDINES BY DECARBOXYLATION OF TETRAHYDRO-1,3-OXAZIN-2-ONES

CROSS REFERENCE TO RELATED APPLICATION

This is a continuation-in-part of application Ser. No. 358,158 filed Mar. 15, 1982, now abandoned.

BACKGROUND OF THE INVENTION

The present invention relates to nitrogen-containing four-membered heterocyclic ring compounds, e.g., azetidines. More particularly the present invention relates to a novel process for preparing such compounds in high yields and purity, and in a simplified manner. Azetidines are a useful class of compounds having beneficial pharmaceutical properties as appetite depressants.

It has been previously known to prepare azetidines via an intermolecular $S_N{}^2$ displacement and cyclization of 1-amino-3-halopropane by reaction with caustic. It is further known to cyclize 1,3-dihalopropane compounds directly by reaction with an appropriate amine. It is further known to prepare azetidines by reduction of 2-azetidinones with strong reducing agents such as LiAlH$_4$. The above processes have been described in greater detail by N. H. Cromwell et al., Chem. Rev., 79 (4), pp. 331–358 (1979).

In U.S. Pat. No. 3,649,618 certain novel 1-(phenylisopropyl)-3,3-dimethyl azetidines having utility as appetite depressants were prepared by reacting an appropriately substituted α-methylphenethyl-3-halo-2,2-disubstituted propionamides with a reducing agent.

SUMMARY OF THE INVENTION

The present invention provides a simplified process for the preparation of azetidines in high yields and purity. Accordingly, azetidines corresponding to the formula:

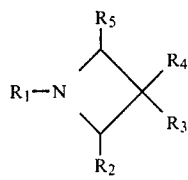

I wherein: $R_1$–$R_5$ each occurrence are independently hydrogen, or alkyl or aryl groups of up to about 20 carbons;
are prepared by contacting a tetrahydro-1,3-oxazin-2-one corresponding to the formula:

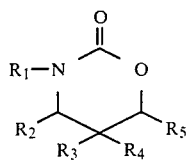

II with a catalytically effective amount of a decarboxylation catalyst under decarboxylation conditions.

DETAILED DESCRIPTION OF THE INVENTION

The tetrahydro-1,3-oxazin-2-ones for use according to the present invention are known compounds or they may be prepared by known techniques. In the past, they have been prepared by the reaction of 1,3-propanolamines with a reactive carbonyl-containing compound such as phosgene (disclosed in U.S. Pat. No. 2,940,971), ethylchloroformate (Berichte, 65B, 385 (1932)), or diethyl carbonate (French patent M1626, CA 58:12576). Tetrahydro-1,3-oxazin-2-ones have also been prepared by the reaction of 1,3-halopropanols with potassium cyanate in a polar solvent such as N,N-dimethylformamide (Japanese Kokai 11,837 (1960)). An additional and preferred process for preparing tetrahydro-1,3-oxazin-2-ones for use according to the present invented process is disclosed in Applicant's copending application Ser. No. 330,743, filed Dec. 14, 1981.

The tetrahydro-1,3-oxazin-2-one is decarboxylated by contacting with a decarboxylation catalyst. Suitable such catalysts are alkali metal salts. Preferred are the alkali metal halides, e.g., lithium, sodium, potassium and cesium fluorides, chlorides, bromides and iodides. A most preferred catalyst is lithium chloride. The catalyst may further comprise inert supportive materials such as alumina, silica, clays, zeolites, etc.

The catalyst is present in a catalytically effective amount. Preferred are amounts from about 0.01 to about 20 molar percent. Most preferred are amounts from about 0.1 to about 10 molar percent. The process may additionally be conducted in a continuous manner by passing a stream containing the tetrahydro-1,3-oxazin-2-one with a catalyst bed and separating the products formed.

Preferred tetrahydro-1,3-oxazin-2-ones for use according to the present invention are those of formula I wherein $R_2$ and $R_5$ are hydrogen. Particularly preferred compounds are those wherein in addition $R_3$ and $R_4$ are both methyl and $R_1$ is $C_{1-4}$ alkyl, phenyl or benzyl. A most preferred compound is tetrahydro-3-benzyl-5,5-dimethyl-1,3-oxazin-2-one.

Suitable decarboxylation conditions are obtained by contacting the tetrahydro-1,3-oxazin-2-one with the decarboxylation catalyst at elevated temperatures from about 150° C. to about 300° C. Preferred are temperatures from about 200° C. to about 250° C. The reaction time may vary from several minutes to several hours depending on the reaction conditions.

The process may be conducted at either elevated or reduced pressures, however, pressures from about 1 torr to atmospheric are preferred. A highly preferred pressure is one at which the azetidine product may be removed from the reaction mixture by distillation as it forms. A stream of an inert gas such as nitrogen is further beneficial in removing volatile products from the reaction mixture.

The reaction may be conducted in a solvent if desired, although for low molecular weight tetrahydro-1,3-oxazin-2-ones, a solvent is not normally required. Inert high boiling liquids such as sulfolane, nitrobenzene, pyrrolidinone, etc., are suitable solvents.

SPECIFIC EMBODIMENTS

Having described the invention, the following examples are provided as further illustrative and are not to be construed as limiting.

EXAMPLE 1

1-Benzyl-3,3-dimethylazetidine

A mixture of 8.97 g (0.04 mole) of tetrahydro-3-benzyl-5,5-dimethyl-1,3-oxazin-2-one and 0.084 g (0.002 mole) of lithium chloride was heated to 245° C. at a pressure of 100 torr in a 25-ml flask equipped with a mechanical stirrer and distillation head. The receiver was cooled with dry ice as the product slowly distilled. After 5 hours, an additional 0.084 g of lithium chloride was added and heating was continued for an additional 25 hours. At this time, 5.84 g (85 percent yield) of pure 1-benzyl-3,3-dimethylazetidine had collected. The material was redistilled at bp 107° C.–108° C. (15 mm).

EXAMPLES 2–5

The following examples were carried out using 0.04 mole of cyclic carbamate and 5 mole percent of catalyst according to the procedure outlined in Example 1.

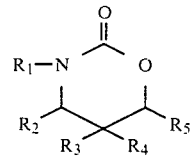

III

| Example | R | Catalyst | Temp (°C.) | Time (hr) | % Yield |
|---|---|---|---|---|---|
| 2 | benzyl | LiBr | 245 | 16 | 70 |
| 3 | CH$_3$ | LiCl | 220 | 8 | 77 |
| 4 | C$_2$H$_5$ | LiCl | 230 | 8 | 84 |
| 5 | C$_6$H$_5$ | LiCl | 245 | 14 | 84 |

What is claimed is:

1. A process for the preparation of azetidines corresponding to the formula:

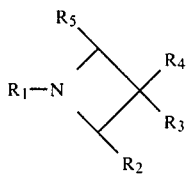

wherein: R$_1$–R$_5$ each occurrence are moieties of up to 10 carbons independently selected from the group consisting of hydrogen, alkyl, and aryl; comprising the step of decarboxylating a tetrahydro-1,3-oxazin-2-one corresponding to the formula:

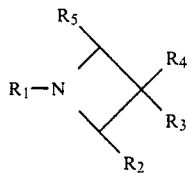

wherein R$_1$–R$_5$ are as previously defined, by contacting with a catalytically effective amount of a decarboxylation catalyst under decarboxylation conditions such that an azetidine is produced.

2. The process of claim 1 wherein the decarboxylation is conducted at a temperature from about 150° C. to about 300° C.

3. The process of claim 2 wherein the decarboxylation is conducted at a temperature from about 200° C. to about 250° C.

4. The process of claim 1 wherein the decarboxylation catalyst is an alkali metal salt.

5. The process of claim 4 wherein the alkali metal salt is an alkali metal halide.

6. The process of claim 5 wherein the alkali metal halide is lithium chloride.

7. The process of claim 1 which is conducted at a pressure from about 1 torr to about atmospheric.

8. A process for the preparation of azetidines corresponding to the formula:

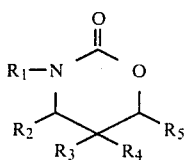

wherein: R$_1$, R$_3$, R$_4$ in each occurrence are moieties of up to 10 carbons independently selected from the group consisting of hydrogen, alkyl, and aryl; R$_2$ and R$_5$ each being hydrogen; comprising the step of decarboxylating a tetrahydro-1,3-oxazin-2-one corresponding to the formula:

wherein R$_1$–R$_5$ are defined as in this claim, by contacting the tetrahydro-1,3-oxazin-2-one with a catalytically effective amount of a decarboxylation catalyst under decarboxylation conditions such that an azetidine is produced.

9. The process of claim 8 wherein R$_3$ and R$_4$ are methyl and R$_1$ is C$_{1-4}$ alkyl, phenyl or benzyl.

* * * * *